United States Patent [19]
Green et al.

[11] Patent Number: 6,048,872
[45] Date of Patent: Apr. 11, 2000

[54] ARYLETHANOLAMINE DERIVATIVES AND THEIR USE AS AGONISTS OF ATYPICAL BETA-ADRENOCEPTORS

[75] Inventors: Richard Howard Green, Stevenage; Michael Walter Foxton, Chalfont St. Giles, both of United Kingdom

[73] Assignee: Glaxo Wellcome Inc., Research Triangle Park, N.C.

[21] Appl. No.: 09/077,910

[22] PCT Filed: Dec. 6, 1996

[86] PCT No.: PCT/EP96/05469

§ 371 Date: Jun. 5, 1998

§ 102(e) Date: Jun. 5, 1998

[87] PCT Pub. No.: WO97/21665

PCT Pub. Date: Jun. 19, 1997

[30] Foreign Application Priority Data

Dec. 8, 1995 [GB] United Kingdom ............... 9525177

[51] Int. Cl.[7] .............. C07D 223/16; C07D 215/00; C07D 209/10; C07D 229/00
[52] U.S. Cl. .............. 514/311; 514/212; 514/415; 514/568; 540/593; 546/165; 548/507; 562/405; 562/442
[58] Field of Search .............. 540/593; 546/165; 548/507; 562/405, 442; 514/311, 212, 415, 568

[56] References Cited

U.S. PATENT DOCUMENTS

| | | | |
|---|---|---|---|
| 4,140,713 | 2/1979 | Oxford | 260/556 |
| 4,154,761 | 5/1979 | Collins | 260/570.5 |
| 4,721,717 | 1/1988 | Friebe | 514/274 |
| 5,576,340 | 11/1996 | Fujita | 514/369 |
| 5,770,615 | 6/1998 | Cheng | 514/365 |

FOREIGN PATENT DOCUMENTS

| | | |
|---|---|---|
| 0 171 689 | 2/1986 | European Pat. Off. . |
| 0 543 662 | 5/1993 | European Pat. Off. . |
| 27 04 895 | 8/1997 | Germany . |
| WO95/33724 | 12/1995 | WIPO . |

*Primary Examiner*—D. Margaret Mach
*Attorney, Agent, or Firm*—Robert H. Brink

[57] ABSTRACT

The present invention relates to phenethanolamine derivatives of formula (I) wherein $R^1$ represents an aryl group optionally substituted by one or more substituents selected from halogen, hydroxy, $C_{1-6}$-alkoxy, $C_{1-6}$-alkyl, nitro, cyano, hydroxymethyl and trifluoromethyl; $R^2$ represents hydrogen or $C_{1-6}$-alkyl; $R^3$ represents a group (A) where the ring is substituted by one to four further substituents selected from $C_{1-6}$-alkyl, halogen, trifluoromethyl, and $C_{1-6}$-alkoxy; or $R^3$ represents a group (B) where the aromatic ring is optionally substituted by up to three further substituents selected from $C_{1-6}$-alkyl, halogen, trifluoromethyl, and $C_{1-6}$-alkoxy; $R^4$ represents hydrogen, or $C_{1-6}$-alkyl; $R^5$ represents $ZCH_2CO_2H$ wherein Z represents a bond, or O; Y represents $(CH_2)_n$ where n is 1–3; and physiologically acceptable derivatives thereof; to process for their preparation; and their use in the treatment of conditions susceptible of amelioration by an atypical beta-adrenoceptor agonist.

13 Claims, No Drawings

ARYLETHANOLAMINE DERIVATIVES AND THEIR USE AS AGONISTS OF ATYPICAL BETA-ADRENOCEPTORS

This application is filed pursuant to 35 U.S.C. §371 as a United States National Phase Application of International Application No. PCT/EP96/05469 filed Dec. 6, 1996 which claims priority from GB 9525177.3 filed Dec. 8, 1995.

This invention relates to a new class of chemical compounds and to their use in medicine. In particular, the invention concerns novel phenethanolamine derivatives, methods for their preparation, pharmaceutical compositions containing them and their use as agonists at atypical beta-adrenoceptors (also known as beta-3-adrenoceptors). Such receptors have been described for example by J R S Arch et. al., *Nature,* 309, 163–165 (1984); C Wilson et. al., *Eur. J. Pharmacol.,* 100, 309–319 (1984); L J Emorine et. al., *Science,* 245, 1118–1121 (1989); and A. Bianchetti et. al. *Br. J. Pharmacol.,* 100, 831–839 (1990). Phenethanolamine derivatives having activity at atypical beta-adrenoceptors are disclosed in, for example, European Patent Applications EP-A-0455006 and EP-A-0543662.

Atypical beta-adrenoceptors belong to the family of adrenoceptors which mediate the physiological actions of the hormones adrenaline and noradrenaline. Sub-types of the adrenoceptors, $\alpha_1$-, $\alpha_2$-, $\beta_1$-, $\beta_2$- and $\beta_3$-(atypical) can be identified on the basis of their pharmacological properties and physiological effects. Chemical agents which stimulate or block these receptors (but not $\beta_3$) are widely used in clinical medicine. More recently, emphasis has been placed upon specific receptor selectivity in order to reduce side effects caused, in part, by interactions with other receptors.

Atypical beta-adrenoceptors are known to occur in adipose tissue and the gastrointestinal tract.

Atypical beta-adrenoceptor agonists have been found to be particularly useful as thermogenic anti-obesity agents and as anti-diabetic agents. Compounds having atypical beta-adrenoceptor agonist activity have also been described as being useful in the treatment of hyperglycaemia, as animal growth promoters, as blood platelet aggregation inhibitors, as positive inotropic agents and as antiatherosclerotic agents, and as being useful in the treatment of glaucoma.

We have now found a novel class of phenylethanolamine derivatives which act as agonists at atypical beta-adrenoceptors. GB 9525177.3, which is the priority document for the present application, describes the syntheses of the compounds of the invention. WO95/33724, which was unpublished at the priority date of the present application, describes the syntheses of compounds which are also of use as agonists at atypical beta-adrenoceptors.

The invention therefore provides, in a first aspect, compounds of formula (I):

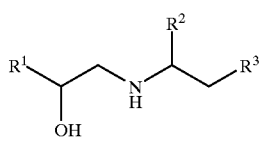

(I)

wherein
$R^1$ represents an aryl group optionally substituted by one or more substituents selected from halogen, hydroxy, $C_{1-6}$alkoxy, $C_{1-6}$alkyl, nitro, cyano, hydroxymethyl and trifluoromethyl;
$R^2$ represents hydrogen or $C_{1-6}$alkyl;
$R^3$ represents a group A

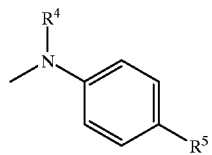

where the ring is substituted by one to four further substituents selected from $C_{1-6}$ alkyl, halogen, trifluoromethyl, and $C_{1-6}$alkoxy;
or $R^3$ represents a group B

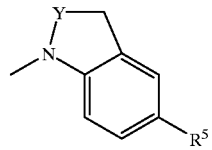

where the aromatic ring is optionally substituted by up to three further substituents selected from $C_{1-6}$alkyl, halogen, trifluoromethyl, and $C_{1-6}$alkoxy;
$R^4$ represents hydrogen, or $C_{1-6}$alkyl;
$R^5$ represents $ZCH_2CO_2H$ wherein Z represents a bond, or O;
Y represents $(CH_2)_n$ where n is 1–3;
and physiologically acceptable derivatives thereof.

Referring to the general formula (I), alkyl includes both straight and branched chain saturated hydrocarbon groups. Similarly, alkoxy includes both straight and branched chain groups.

Referring to the general formula (I), aryl includes monocyclic or bicyclic aromatic carbocyclic groups such as phenyl and naphthyl.

Preferably $R^1$ represents phenyl optionally substituted by one, two or three substituents selected from halogen, hydroxy, $C_{1-6}$alkoxy, $C_{1-6}$alkyl, nitro, cyano, hydroxymethyl and trifluoromethyl. More preferably $R^1$ represents phenyl substituted by a chlorine, fluorine or bromine atom or a methyl or trifluoromethyl group, which atom or group is preferably located in the meta position. Most preferably $R^1$ represents phenyl substituted by a chlorine atom located in the meta position.

$R^2$ is preferably hydrogen or methyl.

Where $R^3$ is group A, preferred substituents are one or more groups selected from halogen, e.g. fluoro or chloro, methyl, trifluoromethyl, and methoxy.

Where $R^3$ is group B, n is preferably 1 or 2 and the aromatic ring has no further substitution.

$R^4$ is preferably hydrogen or methyl.

A preferred sub-class of compounds of formula (I) are those where $R^1$ represents phenyl substituted by a chlorine atom located in the meta position, $R^2$ represents hydrogen or methyl, $R^3$ represents a group A and is substituted by one or more groups selected from halogen, methyl, trifluoromethyl, and methoxy, $R^4$ represents hydrogen or methyl, $R^5$ represents $CH_2CO_2H$, or physiologically acceptable derivatives thereof.

It will be appreciated that the above compounds of formula (I) are optically active. The individual, isolated isomers and mixtures thereof, including racemates, are within the scope of the present invention. Particularly preferred compounds of formula (II) are those wherein the asymmetric carbon atoms in the —CH(OH)— group and the —CH(CH$_3$)— group are in the (R)-configuration.

Suitable compounds of formula (I) of the invention are;
(1-{2-[2-(3-chloro-phenyl)-2R-hydroxyl-ethylamino]-propyl}-2,3-dihydro-1H-indol-5-yl)-acetic acid;
(1-{2-[2-(3-chloro-phenyl)-2R-hydroxyl-ethylamino]-propyl}-1,2,3,4-tetrahydro-quinolin-6-yl)-acetic acid;
(4-{2R-[2-(3-chloro-phenyl)-2R-hydroxyl-ethylamino]-propylamino}-2-methyl-phenyl)-acetic acid;
(4-{2R-[2-(3-chloro-phenyl)-2R-hydroxyl-ethylamino]-propylamino}-3-methyl-phenyl)-acetic acid;
(4-{2R-[2-(3-chloro-phenyl)-2R-hydroxyl-ethylamino]-propylamino}-2-fluoro-phenyl)-acetic acid;
(4-{2R-[2-(3-chloro-phenyl)-2R-hydroxyl-ethylamino]-propyiamino}-3-fluoro-phenyl)-acetic acid;
(4-{2R-[2-(3-chloro-phenyl)-2R-hydroxyl-ethylamino]-propylamino}-2,3-difluoro-phenyl)-acetic acid;
(5-Chloro-4-{2R-[2-(3-chloro-phenyl)-2R-hydroxy-ethylamino]-propylamino}-2-methoxy-phenyl)-acetic acid;
(4-{2-[2-(3-chloro-phenyl)-2R-hydroxyl-ethyiamino]-ethylamino}-2-methyl-phenyl)-acetic acid;
(4-{2-[2-(3-chloro-phenyl)-2R-hydroxyl-ethylamino]-ethylamino}-2,3-difluoro-phenyl)-acetic acid;
(4-{2-[2-(3-chloro-phenyl)-2R-hydroxyl-ethylamino]-ethylamino}-2-trifluoromethyl-phenyl)-acetic acid;
(4-{2R-[2-(3-chloro-phenyl)-2R-hydroxyl-ethylamino]-propylamino}-2,6-difluoro-phenyl)-acetic acid;
(4-{2-[2-(3-chloro-phenyl)-2R-hydroxyl-ethylamino]-ethylamino}-2,3,6-trifluoro-phenyl)-acetic acid;
(4-{2-[2-(3-chloro-phenyl)-2R-hydroxyl-ethylamino]-propylamino}-2-trifluoromethyl-phenyl)-acetic acid;
(4-{2R-[2-(3-Chloro-phenyl)-2R-hydroxyl-ethylamino]-propylamino}-2,3,6-trifluoro-phenyl)-acetic acid;
[2-Chloro-4(2-{[2-(3-chloro-phenyl)-2R-hydroxy-ethyl]-amino}-propylamino)-phenyl]-acetic acid;
[5-Chloro-4-(2R-{[2-(3-chloro-phenyl)-2R-hydroxy-ethyl]-amino}-propylamino)-2-methyl-phenyl]-acetic acid;
(4-{2R-[2-(3-Chloro-phenyl)-2R-hydroxy-ethylamino]-propylamino}-2,6-difluoro-phenoxy)-acetic acid;
(4-{2R-[2-(3-Chloro-phenyl)-2R-hydroxy-ethylamino]-propylamino}-3-trifluoromethyl-phenyl)-acetic acid;
or a physiologically acceptable derivative thereof.

Preferred compounds of the invention include:
(4-{2R-[2-(3-chloro-phenyl)-2R-hydroxyl-ethylamino]-propylamino}-2,3-difluoro-phenyl)-acetic acid;
or a physiologically acceptable derivative thereof.

By "a physiologically acceptable derivative" is meant any physiologically acceptable salt, ester, or salt of such ester, of a compound of formula (I) or any other compound which, upon administration to the recipient, is capable of providing (directly or indirectly) a compound of formula (I) or an active metabolite or residue thereof.

It will be appreciated by those skilled in the art that the compounds of formula (I) may be modified to provide physiologically acceptable derivatives thereof at any of the functional groups in the compounds of formula (I). Of particular interest as such derivatives are compounds modified at the carboxyl function, hydroxyl functions or at amino groups.

It will be appreciated by those skilled in the art that the physiologically acceptable derivatives of the compounds of formula (I) may be derivatised at more than one position.

Preferred physiologically acceptable derivatives of the compounds of formula (I) are pharmaceutically acceptable salts thereof.

Pharmaceutically acceptable salts of the compounds of formula (I) include those derived from physiologically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves physiologically acceptable may be useful in the preparation of salts useful as intermediates in obtaining compounds of the invention and their physiologically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

The compounds of formula (I) act as agonists at atypical beta-adrenoceptors and as such are useful in the treatment of clinical conditions susceptible to amelioration by administration of an atypical beta-adrenoceptor agonist. Such conditions include hyperglycaemia, obesity, hyperlipemia, irritable bowel syndrome and its associated pain, motility dysfunction, excessive gastrointestinal secretion, non-specific diarrhoea, neurogenic inflammation, regulation of intraocular pressure, triglyceridemia, diabetes, e.g. non-insulin-dependent diabetes mellitus (NIDDM or Type II), such as obese NIDDM and non-obese NIDDM, diabetic complications such as retinopathy, nephropathy, neuropathy, cataracts, coronary heart diseases and arteriosclerosis, osteoporosis; and gastrointestinal disorders, particularly inflammatory gastrointestinal disorders.

Accordingly the present invention provides a method of treatment of a mammal, including man, suffering from condition susceptible of amelioration by an atypical beta-adrenoceptor agonist which method comprises administering to the subject an effective amount of a compound of general formula (I) or a physiologically acceptable derivative thereof.

References in this specification to treatment include prophylactic treatment as well as the alleviation of symptoms.

In a further aspect, the invention provides the use of a compound of general formula (I) or a physiologically acceptable salt or solvate thereof, for the manufacture of a medicament for the treatment of a condition susceptible of amelioration by an atypical beta-adrenoceptor agonist.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a physiologically acceptable derivative thereof together with one or more physiologically acceptable carriers therefor and, optionally, other therapeutic and/or prophylactic ingredients. The carrier(s) or excipient(s) must be "acceptable" in the sense of being compatible with the other ingredients of the formulation and not deleterious to the recipient thereof.

Thus the compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins, or as sparingly soluble derivatives, for example, as a sparingly soluble salt.

A proposed dose of the compounds according to the present invention for administration to a human (of approximately 70 kg body weight) is 0.1 mg to 1 g, preferably to 1 mg to 100 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated.

The precise dose and route of administration will ultimately be at the discretion of the attendant physician or veterinarian.

The compounds of the invention may be prepared by any of the processes known in the art for the preparation of similar compounds.

For example, according to process (A), compounds of formula (I) may be prepared by reaction of a compound of formula (Ia)

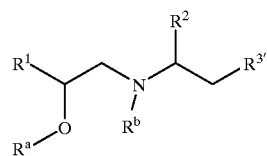

(Ia)

wherein $R^1$, $R^2$, and, are as defined as for formula (I), $R^3$ represents $R^3$ where the acidic group is protected by an alkyl ester, and $R^a$ and $R^b$ are protecting groups, by deprotection of the protecting groups in a suitable mixture such as 6M hydrochloric acid in tetrahydrofuran.

According to process (B), compounds of formula (I) may be prepared by reaction of a compound of formula (II) with a compound of formula (III):

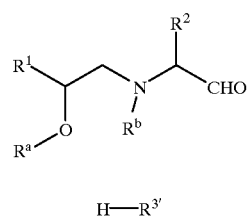

(II)

(III)

wherein $R^1$, $R^2$, $R^3$, $R^a$, and $R^b$ are as defined above, in the presence of a reducing agent, followed by removal of the protecting groups.

Compounds of formula (II) may be prepared by reaction of compounds of formula (IV), with an amine acid salt of formula (V).

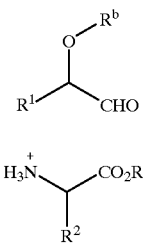

(IV)

(V)

wherein $R^1$, $R^2$, and $R^b$ are as defined herein before, and $R^c$ is a suitable alkyl group for protection, in the presence of a reducing agent. Following protection of the nitrogen, the ester is reduced by a suitable reducing agent such as di-isobutyl aluminium hydride.

Where $R^3$ is group A, compounds of formula (III) may be prepared from compounds of formula (VI)

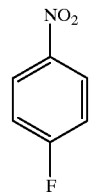

(VI)

where the aromatic ring is optionally substituted as defined for $R^3$, by treatment with a mixed ester, e.g. methyl, benzyl, of malonic acid at elevated temperature in a suitable solvent such as N,N dimethylformamide, followed by treatment with a suitable reducing agent.

Suitable reducing agents of use in the reactions include hydrogen in the presence of a catalyst, such as a noble metal catalyst, for example palladium, platinum or platinum oxide, Raney-nickel or hydride reducing agents such as borohydrides, for example sodium borohydride sodium triacetoxyborohydride or sodium cyanoborohydride. Suitable reaction conditions will be readily apparent to those skilled in the art and are further illustrated by the accompanying examples.

Compounds of formula (III) where $R^3$ represents group B, (IV), (V) and (VI) are known compounds or may be prepared from known compounds by standard procedures well known to those skilled in the art.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene and P M G Wuts (John Wiley and Sons 1991).

Conventional amino protecting groups may include for example aralkyl groups, such as benzyl, diphenylmethyl or triphenylmethyl groups; and acyl groups such as N-benzyloxycarbonyl or t-butoxycarbonyl.

Conventional oxygen protecting groups may include for example alky silyl groups, such as trimethylsilyl, or tert-butyldimethylsilyl; alkylethers such as tetrahydropyranyl, or tert-butyl; or esters such as acetate.

Removal of any protecting groups present may be achieved by conventional procedures.

Atypical beta-adrenoceptor agonists are compounds which demonstrate a pharmacological response mediated at atypical beta-adrenoceptors. This activity has been be measured as the ability to stimulate lipolysis by rat adipocytes at sub-micromolar concentrations, in a response that is resistant to blockade by standard beta-adrenoceptor blocking drugs such as propranolol.

A particularly useful method for determining agoinst activity at human atypical beta-adrenoceptors involves the use of Chinese hamster ovarian (CHO) cells transfected with the human beta-3-adrenoceptor according to Method 2. The cell lines may also be transfected with human beta-1- and beta-2- adrenoceptor in a similar manner to provide a method of determining the selectivity of the compounds of the invention at the three receptors.

METHOD 1

Cell Culture

General cell culture guidelines are observed (Fershney, R. A. (1987) Culture of animal cells: A manual of basic technique. Wiley-Liss, Inc., N.Y.). A standard cell culture incubator is used (37° C., 5% $CO_2$ in air, 95% relative humidity). H $\beta_3$CHO cells are grown in 75 ml flasks in MEMα medium containing 9% FCS & 125 µg/ml G418. One confluent flask of cells is trypsinised and resuspended in 80 ml of culture medium; 1 ml of the cell suspension is added to each well of three 24-well plates. The plates are then incubated for 1 day.

Experimental method:

The medium is aspirated from each well, and the well rinsed with phosphate-buffered saline (PBS, this is then aspirated). 1 ml of MEMα (no FCS or G418, 300µ M IBMX) is added to each well. Antagonists, if required, are added at this stage. The plate is then placed back in the incubator for 30 min. Drugs are then added to the wells (10 µl, 100x required final concentration), the plate gently swirled to mix the drugs, and the plate placed back in the incubator for 30 min. The medium is then aspirated from each well, the well rinsed with PBS, and 0.5 ml perchloric acid (6% v/v in distilled water, 2–5° C.). The plate is left on ice for 30 min. The perchloric acid (containing cAMP) is transferred to a clean 24-well plate and the acid neutralised by addition of saturated $KHCO_3$ solution (200 µl) to each well. The plate is then swirled and frozen (−20° C.) until cAMP is assayed. cAMP is assayed using an enzyme-immunoassay kit (Amersham).

The relative potency of each test agonist (EPMR) is compared to isoprenaline as follows:

$$EPMR = \frac{EC_{50} \text{ agonist}}{EC_{50} \text{ isoprenaline}}$$

wherein $EC_{50}$ is the molar concentration of agonist which produces 50% of the maximum possible response for that agonist.

Using the non-selective beta-adrenoceptor agonist isoprenaline as a reference agonist, compounds selective for atypical beta-adrenoceptors should preferably be a minimum of 10–30 times less potent than isoprenaline at $\beta_1$- or $\beta_2$-adrenoceptors and, more preferably, 300–1000 times less potent than isoprenaline at $\beta_1$- or $\beta_2$-adrenoceptors.

An experimental model in which atypical beta-adrenoceptor agonists may be shown to be of use in the treatment of gastrointestinal disorders is described below as Method 3. The procedure is based upon that described by H. Satoh et. al., *Gastroenterology*, 81, 719–725 (1981) in which the effect of compounds on indomethacin-induced gastric antral lesions in the re-fed rat is investigated. Indomethacin is an example of the class of compound known as non-steroidal anti-inflammatory drugs (NSAIDs), the use of which is frequently associated with gastrointestinal ulcers.

METHOD 2

Food (but not water) is withheld from female random hooded rats (70–120 g) for 24 hours and then the rats are re-fed with Rat and Mouse No. 1 Maintenance Diet. After 1 hour of access to food, the rats are dosed orally with either the test compound or solvent (0.5% w/v methyl cellulose in water). 30 minutes later, indomethacin (60 mg/kg; dissolved in 1% w/v $NaHCO_3$ in saline) is administered as a single subcutaneous injection at the back of the neck. Subsequently, the rats are allowed food, but water is withheld, and the animals are humanely killed by cervical dislocation at 6 hours post dose. Control animals received a single subcutaneous dose of the appropriate solvent.

The rat's stomach is removed (with a small amount of duodenum attached), opened along the greater curvature and the contents removed by washing with 0.9% w/v sodium chloride solution (saline). The opened stomach is pinned out (mucosal surface uppermost) on a polystyrene mat and the area of damage assessed by placing a grid (composed of 1 mm squares) over the antral region. Antral damage appears as discrete black or dark brown ulcers. The total area of antral damage is then expressed as a percentage of the total surface area of the antrum.

The protective effect of the test compound on indomethacin-induced antral damage is calculated as a percentage using the following equation:

$$100 \times \frac{\text{\% area of damage NSAID} - \text{\% area of damage NSAID + test compound}}{\text{\% area of damage with NSAID}}$$

The invention is further illustrated by the following intermediates and examples. All temperatures are in degrees centigrade.

INTERMEDIATE 1
(R)-(3-chloro-phenyl)-hydroxy-acetic acid methyl ester

A solution of (R)-(3-chloro-phenyl)-hydroxy-acetic acid (19.98 g) in methanol (250 ml) containing concentrated sulphuric acid (1 ml) was heated under reflux for 6.5 h. The solution was cooled, neutralised with aqueous sodium bicarbonate solution, and concentrated. The residue was dissolved in ethyl acetate, washed with aqueous sodium bicarbonate solution, dried, and evaporated to give the title compound (21.13 g) as a pale-yellow oil.

$[a]_D$ –104° (c 1.00 MeOH)

INTERMEDIATE 2
(R)-(3-chloro-phenyl)-(tert-butyl-dimethyl-silanoxy)-acetic acid methyl ester A solution of (R)-(3-chloro-phenyl)-hydroxy-acetic acid methyl ester (21.0 g), imidazole (14.25 g), and tert-butyldimethylsilyl chloride (25.0 g) in N,N-dimethylformamide (250 ml) was stirred at room temperature for 18 h. The mixture was poured into water (2.5 l) and extracted with ethyl acetate. The combined extracts were washed with water and saturated brine, dried, and concentrated. The residue was purified by flash chromatography, eluting with cyclohexane:ethyl acetate (9:1) to give the title compound as a colourless oil (32.63 g).

$[a]_D$ –55.4° (c 1.21 MeOH)

INTERMEDIATE 3
(R)-(3-chloro-phenyl)-(tert-butyl-dimethyl-silanoxy)-acetaldehyde To a stirred solution of (R)-(3-chloro-phenyl)-(tert-butyl-dimethyl-silanoxy)-acetic acid methyl ester (4.0 g) in anhydrous ether (10 ml) and maintained at <–65° was added dropwise a 1.5M solution of di-isobututylaluminium hydride in toluene (10 ml). When addition was complete the solution was stirred at –65° for a further hour, then quenched with methanol (10 ml). The mixture was allowed to attain room temperature when silica (20 g) was added. Solvent was removed under reduced pressure, and the residue was purified by flash chromatography, eluting with cyclohexane:ethyl acetate (9:1) to give the title compound as a colourless liquid (3.1 g).

$[a]_D$ –45.3° (c 1.50 MeOH)

INTERMEDIATE 4
2R-[2R-(tert-Butyl-dimethyl-silanyloxy)-2-(3-chloro-phenyl)-ethylamino]-propionic acid methyl ester (R)-(3-chloro-phenyl)-(tert-butyl-dimethyl-silanoxy)-acetaldehyde (2.32 g) was added to a stirred solution of (R)-2-aminopropionic acid methyl ester hydrochloride (1.13 g) in dichloromethane (50 ml). The solution was stirred for 15 min, then sodium triactetoxyborohydride (3.45 g) was added, and the mixture was stirred a further 18 h. The solution was washed with aqueous sodium bicarbonate solution, then the organic phase was dried and concentrated. The residue was purified by chromatography, eluting with cyclohexane:ethyl acetate (9:1) to give the title compound as a colourless oil (2.42 g)

$[a]_D$ –29.4° (c 1.36 MeOH)

Similarly prepared was:

INTERMEDIATE 5
[2R-(tert-Butyl-dimethyl-silanyloxy)-2-(3-chloro-phenyl)-ethylamino]-acetic acid methyl ester as a colourless oil (1.26 g), Assay: Found: C 56.9; H 7.95; N 3.9% $C_{17}H_{28}ClNO_3Si$ requires C 57.1; H 7.8; N 3.9% from amino-acetic acid methyl ester hydrochloride (1.05 g) and (R)-(3-chloro-phenyl)-(tert-butyl-dimethyl-silanoxy)-acetaldehyde (2.16 g).

INTERMEDIATE 6
{2R-(tert-Butoxycarbonyl)-[2R-(tert-butyl-dimethyl-silanyloxy)-2-(3-chloro-phenyl)-ethyl]-amino}-propionic acid methyl ester A mixture of 2R-[2R-(tert-butyl-dimethyl-silanyloxy)-2-(3-chloro-phenyl)-ethylamino]-propionic acid methyl ester (2.15 g) and di-t-butyl pyrocarbonate (1.37 g) was heated at 80–100° for 1 h. The mixture was cooled and purified by chromatography eluting with cyclohexane:ethyl acetate (19:1) to give the title compound as a colourless oil (2.70 g).

Assay: Found: C 58.4; H 8.1; N 3.0% $C_{23}H_{38}ClNO_5Si$ requires C 58.5; H 8.1; N 3.0%

Similarly prepared was:

INTERMEDIATE 7
{(tert-Butoxycarbonyl)-[2R-(tert-butyl-dimethyl-silanyloxy)-2-(3-chloro-phenyl)-ethyl]-amino}-acetic acid methyl ester as a colourless oil (1.55 g) from [2R-(tert-butyl-dimethyl-silanyloxy)-2-(3-chloro-phenyl)-ethylamino]-acetic acid methyl ester (1.20 g)

$[a]_D$ –25.2° (c 1.3 MeOH)

INTERMEDIATE 8
{2R-(tert-Butoxycarbonyl)-[2R-(tert-butyl-dimethyl-silanyloxy)-2-(3-chloro-phenyl)-ethyl]-amino}-propionaldehyde 1.5M di-isobutylaluminium hydride in toluene (8.1 ml) was added dropwise to a stirred, cooled solution of the {2R-(tert-butoxycarbonyl)-[2R-(tert-butyl-dimethyl-silanyloxy)-2-(3-chloro-phenyl)-ethyl]-amino}-propionic acid methyl ester (2.30 g) in toluene (50 ml) at such a rate that the reaction temperature did not rise above –70°. The solution was stirred 1 h at this temperature, then quenched with methanol (10 ml). The mixture was preabsorbed on silica and purified by chromatography eluting with cyclohexane:ethyl acetate (9:1) to give the title compound as a colourless oil (1.45 g).

$C_{22}H_{36}ClNO_4Si$: MH$^+$ 443

Similarly prepared was:

INTERMEDIATE 9
{(tert-Butoxycarbonyl)-[2R-(tert-butyl-dimethyl-silanyloxy)-2-(3-chloro-phenyl)-ethyl]-amino}-acetaldehyde as a colourless gum (0.37 g), n.m.r. (CDCl$_3$): d -0.15 (d, 3H), 0.05 (d, 3H), 0.90 (s, 9H), 1.45 (d, 9H), 2.9–3.2 (m, 1H), 3.4–3.65 (m, 1H), 3.70 (s, 3H), 3.75–4.15 (m, 2H), 4.8–5.0 (m, 1H), 7.05–7.35 (m, 4H).

from {(tert-butoxycarbonyl)-[2R-(tert-butyl-dimethyl-silanyloxy)-2-(3-chlorophenyl)-ethyl]-amino}-acetic acid methyl ester (0.50 g).

INTERMEDIATE 10
(2,3-Dihydro-1H-indol-5-yl)-acetic acid methyl ester

A suspension of (1-acetyl-2,3-dihydro-1H-indol-5-yl)-acetic acid methyl ester (0.60 g) in 2M hydrochloric acid (15 ml) was heated under reflux for 5 h. The mixture was evaporated to dryness. The residue was dissolved in methanol (20 ml) and treated with concentrated sulphuric acid (5 drops). The solution was stirred at room temperature for one hour, then concentrated. The residue was partitioned between ethyl acetate and sodium carbonate solution. The organic phase was dried and evaporated and the residue purified by chromatography eluting with cyclohexane:ethyl acetate (2:1) to give the title compound as a brown oil (0.40 g).

Assay Found: C 68.9; H 6.6; N 7.2% $C_{11}H_{13}NO_2$ requires C 69.1; H 6.8; N 7.3%

INTERMEDIATE 11
(4-Amino-2-methyl-phenyl)-acetic acid methyl ester

Sodium hydride (1.29 g of 60% dispersion in oil) was added portionwise to a stirred solution of malonic acid, methyl benzyl ester (5.84 ml) in dry N,N-dimethylformamide (40 ml). After 2.5 h 2-fluoro-5-nitrotoluene (5.0 g) was added, and the mixture was warmed to 100° for 18 h. The mixture was cooled then partioned between ethyl acetate and water. The aqueous phase was separated and extracted further with ethyl acetate. The combined organic extracts were dried, concentrated, and purified by chromatography eluting with cyclohexane:ethyl acetate (6:1) to give 2-(2-methyl-4-nitro-phenyl)-malonic acid benzyl ester methyl ester, admixed with the starting malonate ester, as a yellow oil (4.60 g).

The crude mixture (4.2 g), ammonium formate (7.1 g), and 10% palladium on carbon (0.45 g) in methanol (150 ml) was heated under reflux for 2 h under an atmosphere of nitrogen. The mixture was cooled, filtered, and the filtrate was concentrated. Chromatography of the residue eluting with cyclohexane:ethyl acetate (2:1) gave the title compound (1.55 g) as a yellow oil.

Assay Found: C 66.55; H 7.6; N 7.6% $C_{10}H_{13}NO_2$ requires C 67.0; H 7.3; N 7.8% n.m.r. ($CDCl_3$): d values include 2.22 (s, 3H), 3.55 (s, 2H), 3.59 (broad s, 2H), 3.68 (s, 3H), 6.51 (s+d, 2H), 6.98 (d, 1H)

Similarly prepared were:

INTERMEDIATE 12
(4-Amino-3-methyl-phenyl)-acetic acid methyl ester as a pale brown oil (0.901 g), n.m.r. ($CDCl_3$): d values include 2.12 (s, 3H), 3.49 (s, 2H), 3.58 (broad s, 2H), 3.66 (s, 3H), 6.60 (d, 1H), 6.92 (s+d, 2H).

from 5-fluoro-2-nitrotoluene (2.5 g) and malonic acid, benzyl ester methyl ester (5.84 ml)

INTERMEDIATE 13
(4-Amino-2-fluoro-phenyl)-acetic acid methyl ester as a pale brown oil (1.43 g)

n.m.r. ($CDCl_3$): d values include 3.57 (s, 2H), 3.74 (broad s, 2H), 3.69 (s, 3H), 6.32–6.49 (m, 2H), 7.00 (t, 1H).

from 3,4-difluoro-nitrobenzene (3.48 ml) and malonic acid, benzyl ester methyl ester (5.69 ml)

INTERMEDIATE 14
(4-Amino-3-fluoro-phenyl)-acetic acid methyl ester as a yellow oil (0.34 g)

n.m.r. ($CDCl_3$): d values include 3.50 (s, 2H), 3.69 (s, 3H), 6.66–6.90 (m, 3H).

from 2,4-difluoro-nitrobenzene (3.33 ml) and malonic acid, benzyl ester methyl ester (6.0 ml)

INTERMEDIATE 15
(4-Amino-2,3-difluoro-phenyl)-acetic acid methyl ester as a pale yellow oil (1.08g), n.m.r. ($CDCl_3$): d values include 3.59 (s, 2H), 3.71 (s, 3H), 3.80 (broad s, 2H), 6.50 (t, 1H), 6.78 (t, 1H)

from 2,3,4-trifluoro-nitrobenzene (3.59 ml) and malonic acid, benzyl ester methyl ester (5.69 ml)

INTERMEDIATE 16
(4-Amino-2,3,6-trifluoro-phenyl)-acetic acid methyl ester as colourless crystals (1.35 g)

n.m.r. ($CDCl_3$): d values include 3.72 (s, 3H), 3.60 (s, 2H), 6.30 (m, 1H).

from 2,3,4,6-tetrafluoro-nitrobenzene (3.23 g) and malonic acid, benzyl ester methyl ester (3.63 g).

INTERMEDIATE 17
(4-Amino-2-bromo-phenyl)-acetic acid methyl ester as a yellow oil (0.104 g)

n.m.r. ($CDCl_3$): d values include 3.69 (s, 2H), 3.71 (s, 3H), 6.59 (dd, 1H), 6.86 (m, 1H), 7.06 (d, 1H), from 3-bromo-4-fluoro-nitrobenzene (6.91 g) and malonic acid, benzyl ester methyl ester (5.69 ml)

INTERMEDIATE 18
(4-Amino-2-trifluoromethyl-phenyl)-acetic acid methyl ester

A solution of (4-amino-2-trifluoromethyl-phenyl)-acetic acid (0.082 g) in methanol (10 ml) containing concentrated sulphuric acid (0.1 ml) was heated under reflux for 2 h. The solution was cooled, concentrated, and partitioned between ethyl acetate and aqueous sodium carbonate solution. The organic phase was separated, dried, and concentrated to give the title compound as a yellow solid (0.089 g)

$C_{10}H_{10}F_3NO_2$: $MH^+$ 234

INTERMEDIATE 19
[1-(2-{tert-Butoxycarbonyl-[2R-(tert-butyl-dimethyl-silanoxy)-2-(3-chloro-phenyl)-ethyl]-amino}-propyl)-2,3-dihydro-1H-indol-5-yl]-acetic acid methyl ester A solution of (2,3-dihydro-1H-indol-5-yl)-acetic acid methyl ester (0.10 g) and {2R-(tert-butoxycarbonyl)-[2R-(tert-butyl-dimethyl-silanyloxy)-2-(3-chloro-phenyl)-ethyl]-amino}-propionaldehyde (0.20 g) in dichloromethane (15 ml) containing acetic acid (0.031 ml) was stirred at room temperature for 40 min, then the reaction mixture was cooled to 0°, and sodium triacetoxyborohydride (0.19 g) was added. The mixture was stirred at room temperature for two days, then washed with aqueous sodium bicarbonate solution. The organic phase was dried, concentrated, and the residue purified by chromatography eluting with cyclohexane:ethyl acetate (9:1) to give the title compound as a yellow gum (0.22 g)

Assay Found: C 64.1; H 7.6; N 4.4% $C_{33}H_{49}ClN_2O_5$ requires C 64.2; H 7.95; N 4.5%

Chiral HPLC and n.m.r. confirm the compound to be a mixture of RR and RS isomers (1:1).

Similarly prepared were:

INTERMEDIATE 20
[1-(2{-tert-Butoxycarbonyl-[2R-(tert-butyl-dimethyl-silanoxy)-2-(3-chloro-phenyl)-ethyl]-amino}-propyl)-1,2,3,4-tetrahydro-quinolin-6-yl]-acetic acid methyl ester as a yellow oil (0.51 g)

n.m.r. ($CDCl_3$): d values include 0.88 (s, 9H), 3.46 (s, 2H), 3.67 (s, 3H), 6.84 (broad s, 1H), 6.91 (d, 2H), $C_{34}H_{51}ClN_2O_5Si$: $MH^+$ 631 from (1,2,3,4-tetrahydro-quinolin-6-yl)-acetic acid methyl ester (0.20 g) and {2R-(tert-butoxycarbonyl)-[2R-(tert-butyl-dimethyl-silanyloxy)-2-(3-chloro-phenyl)-ethyl]-amino}-propionaldehyde (0.55 g).

INTERMEDIATE 21
[4-(2-{tert-Butoxycarbonyl-[2-(tert-butyl-dimethyl-silanyloxy)-2-(3-chloro-phenyl)-ethyl]-amino}-propylamino)-2-methyl-phenyl]-acetic acid methyl ester as a pale yellow oil (0.22 g), Assay Found: C 63.2; H 8.6; N 4.7% $C_{32}H_{49}ClN_2O_5Si$ requires C 63.5; H 8.2; N 4.6%
from 4-amino-2-methyl-phenylacetic acid methyl ester (0.11 g) and {2R-(tert-butoxycarbonyl)-[2R-(tert-butyl-dimethyl-silanyloxy)-2-(3-chloro-phenyl)-ethyl]-amino}-propionaldehyde (0.25 g).

INTERMEDIATE 22
[4-(2R-{tert-Butoxycarbonyl-[2R-(tert-butyl-dimethyl-silanyloxy)-2-(3-chloro-phenyl)-ethyl]-amino}-propylamino)-3-methyl-phenyl]-acetic acid methyl ester as a pale yellow gum (0.25 g), Assay Found: C 63.4; H 8.2; N 4.45% $C_{32}H_{49}ClN_2O_5Si$ requires C 63.5; H 8.2; N 4.6%
from 4-amino-3-methylphenyl-acetic acid methyl ester (0.10 g) and {2R-(tert-butoxycarbonyl)-[2R-(tert-butyl-dimethyl-silanyloxy)-2-(3-chloro-phenyl)-ethyl]-amino}-propionaldehyde (0.25 g)

INTERMEDIATE 23
[4-(2R-{tert-Butoxycarbonyl-[2R-(tert-butyl-dimethyl-silanyloxy)-2-(3-chloro-phenyl)-ethyl]-amino}-propylamino)-2-fluoro-phenyl]-acetic acid methyl ester as a colourless oil (0.25 g), Assay Found: C 61.1; H 7.8; N 4.4% $C_{31}H_{46}ClFN_2O_5Si$ requires C 61.1; H 7.6; N 4.6%
from 4-amino-2-fluoro-phenylacetic acid methyl ester (0.10 g) and {2R-(tert-butoxycarbonyl)-[2R-(tert-butyl-dimethyl-silanyloxy)-2-(3-chloro-phenyl)-ethyl]-amino}-propionaldehyde (0.25 g)

INTERMEDIATE 24
[4-(2R-{tert-Butoxycarbonyl-[2R-(tert-butyl-dimethyl-silanyloxy)-2-(3-chloro-phenyl)-ethyl]-amino}-propylamino)-3-fluoro-phenyl]-acetic acid methyl ester as a pale yellow gum (0.56 g), Assay Found: C 61.2; H 7.8; N 4.7% $C_{31}H_{46}ClFN_2O_5Si$ requires C 61.1; H 7.6; N 4.6%
from 4-amino-3-fluoro-phenylacetic acid methyl ester (0.27 g) and {2R-(tert-butoxycarbonyl)-[2R-(tert-butyl-dimethyl-silanyloxy)-2-(3-chloro-phenyl)-ethyl]-amino}-propionaldehyde (0.66 g)

INTERMEDIATE 25
[4-[2R-{tert-Butoxycarbonyl-[2R-(tert-butyl-dimethyl-silanyloxy)-2-(3-chloro-phenyl)-ethyl]-amino}-propylamino)-2,3-difluoro-phenyl]-acetic acid methyl ester as a colourless oil (0.50 g), Assay Found: C 59.9; H 7.4; N 4.4% $C_{31}H_{45}ClF_2N_2O_5Si$ requires C 59.4; H 7.2; N 4.5%
from 4-amino-2,3-difluoro-phenylacetic acid methyl ester (0.3 g) and {2R-(tert-butoxycarbonyl)-[2R-(tert-butyl-dimethyl-silanyloxy)-2-(3-chloro-phenyl)-ethyl]-amino}-propionaldehyde (0.50 g).

INTERMEDIATE 26
[4-(2R-{tert-Butoxycarbonyl-[2R-(tert-butyl-dimethyl-silanyloxy)-2-(3-chloro-phenyl)-ethyl]-amino}-propylamino)-5-chloro-2-methoxy-phenyl]-acetic acid methyl ester as a colourless oil (0.04 g), $C_{32}H_{68}Cl_2N_2O_6Si$: MH$^+$ 656
from 4-amino-5-chloro-2-methoxy-phenylacetic acid, methyl ester (0.05 g) and {2R-(tert-butoxycarbonyl)-[2R-(tert-butyl-dimethyl-silanyloxy)-2-(3-chloro-phenyl)-ethyl]-amino}-propionaldehyde (0.1 g).

INTERMEDIATE 27
[4-(2-{tert-Butoxycarbonyl-[2R-(tert-butyl-dimethyl-silanyloxy)-2-(3-chloro-phenyl)-ethyl]-amino}-ethylamino)-2-methyl-phenyl]-acetic acid methyl ester as a yellow gum $C_{31}H_{47}ClN_2O_5$: MH$^+$ 591
from (4-amino-2-methyl-phenyl)-acetic acid methyl ester (0.20 g) and {2R-(tert-butoxycarbonyl)-[2R-(tert-butyl-dimethyl-silanyloxy)-2-(3-chloro-phenyl)-ethyl]-amino}-acetaldehyde (0.525 g)

INTERMEDIATE 28
[4-(2-{tert-Butoxycarbonyl-[2R-(tert-butyl-dimethyl-silanyloxy)-2-(3-chloro-phenyl)-ethyl]-amino}-ethylamino)-2-trifluoromethyl-phenyl]-acetic acid methyl ester as a colourless gum $C_{31}H_{44}F_3ClN_2O_5$: MH$^+$ 645
from (4-amino-2-trifluoromethyl-phenyl)-acetic acid methyl ester (0.087 g) and {2R-(tert-butoxycarbonyl)-[2R-(tert-butyl-dimethyl-silanyloxy)-2-(3-chloro-phenyl)-ethyl]-amino}-acetaldehyde (0.224 g).

INTERMEDIATE 29
[4-(2R-{tert-Butoxycarbonyl-[2R-(tert-butyl-dimethyl-silanyloxy)-2-(3-chloro-phenyl)-ethyl]-amino}-propylamino)-2-trifluoromethyl-phenyl]-acetic acid methyl ester as a colourless gum (0.307 g)

$C_{31}H_{44}F_3ClN_2O_5$: MH$^+$ 659
from (4-amino-2-trifluoromethyl-phenyl)-acetic acid methyl ester (0.150 g) and {2R-(tert-butoxycarbonyl)-[2R-(tert-butyl-dimethyl-silanyloxy)-2-(3-chloro-phenyl)-ethyl]-amino}-acetaldehyde (0.313 g).

INTERMEDIATE 30
[4-(2-{tert-Butoxycarbonyl-[2R-(tert-butyl-dimethyl-silanyloxy)-2-(3-chloro-phenyl)-ethyl]-amino}-ethylamino)-2,3-difluoro-phenyl]-acetic acid methyl ester as a colourless gum (0.12 g)

n.m.r. (CDCl$_3$): d values include −0.11 (s, 3H), 0.03 (3, 3H), 0.88 (s, 9H), 3.56 (s, 2H), 3.70 (s, 3H), 6.35 (t, 1H), 6.81 (t, 1 H), 7.37 (broad s, 1H).
from (4-amino-2,3-difluoro-phenyl)-acetic acid methyl ester (0.10 g) and {2R-(tert-butoxycarbonyl)-[2R-(tert-butyl-dimethyl-silanyloxy)-2-(3-chloro-phenyl)-ethyl]-amino}-acetaldehyde (0.30 g).

INTERMEDIATE 31
[4-(2R-{tert-Butoxycarbonyl-[2R-(tert-butyl-dimethyl-silanyloxy)-2-(3-chloro-phenyl)-ethyl]-amino}-propylamino)-2,3,6-trifluoro-phenyl]-acetic acid methyl ester as a colourless gum (0.293 g), n.m.r. (CDCl$_3$): d values include −0.11 (s, 3H), 0.032 (s, 3H), 0.88 (s, 9H), 3.02–3.29 (m, 4H), 3.59 (s, 2H), 3.71 (s, 3H), 6.17 (m, 1H),
from {2R-(tert-Butoxycarbonyl)-[2R-(tert-Butyl-dimethyl-silanyloxy)-2-(3-chloro-phenyl)-ethyl]-amino}-propionaldehyde (0.83g) and (4-Amino-2,3,6-trifluoro-phenyl)-acetic acid methyl ester (0.33 g)

INTERMEDIATE 32
[4-(2R-{tert-Butoxycarbonyl-[2R-(tert-butyl-dimethyl-silanyloxy)-2-(3-chloro-phenyl)-ethyl]-amino}-propylamino)-2-chloro-phenyl]-acetic acid methyl ester as a yellow oil (400 mg), from {2R-(tert-butoxycarbonyl)-[2R-

(tert-butyl-dimethyl-silanoxy)-2-(3-chloro-phenyl)-ethyl]-amino}propionaldehyde (0.36 g, 0.8 mmol) and (4-amino-2chloro-phenyl)acetic acid methyl ester (0.23 g, 1.19 mmol)

INTERMEDIATE 33

[4-(2R-{tert-Butoxycarbonyl-[2R-(tert-butyl-dimethyl-silanyloxy)-2-(3-chloro-phenyl)-ethyl]-amino}-propylamino)-5-chloro-2-methyl-phenyl]-acetic acid methyl ester as a colorless oil (230 mg)

from {2R-(tert-butoxycarbonyl)-[2R-(tert-butyl-dimethyl-silanoxy)-2-(3-chloro-phenyl)-ethyl]-amino}propionaldehyde (0.35 g) and (4-amino-2-methyl-3-chloro-phenyl)acetic acid methyl ester (0.26 g).

INTERMEDIATE 34

(4-{2R-{tert-Butoxycarbonyl-[2R-(tertbutyl-dimethyl-silanyloxy)-2-(3-chloro-phenyl)-ethyl]-amino}-propylamino)-2,6-difluoro-phenyoxy)-acetic acid methyl ester(454 mg), TLC (2:1 hexanes: ethyl acetate) Rf 0.6
from (4-amino-2,6-difluoro-phenyoxy)-acetic acid methyl ester (314 mg) and {2R-(tert-butoxycarbonyl)-[2R-(tert-butyl-dimethyl-silanyloxy)-2-(3-chloro-phenyl)-ethyl]-amino}-propionaldehyde (380 mg)

INTERMEDIATE 35

2-(4-nitro-2chlorophenyl)-malonic acid dimethyl ester

3-Chloro-4-fluoronitobenzene (1.9 g) and dimethylmalonate (1.26 mL) were dissolved in N-methylpyrrolidinone (50 mL). Sodium hydroxide (0.92 g) was added and the solution heated at 80° for 2 h. The reaction was cooled and 1 N hydrochloric acid added. The mixture was extracted with ethyl acetate, concentrated and the residue purified by chromatography on silica gel eluting with hexane/ethyl acetate (9:1) to give the title compound (2.45 g)

INTERMEDIATE 36

2-(4 nitro-2-chlorophenyl)acetic acid methyl ester 2-(4-nitro-2chlorophenyl)-malonic acid dimethyl ester was dissolved in DMSO, then lithium chloride (0.759 g), and water (0.15 mL) were added. The mixture was heated to 100° C. for 3h. The reaction was cooled and the product purified by chromatography on silica gel eluting with hexane/ethyl acetate (9:1) to give the title compound as a yellow oil (1.77 g).

INTERMEDIATE 37

(4-Amino-2-chloro-phenyl)-acetic acid methyl ester 2-(4 nitro-2-chlorophenyl )acetic acid methyl ester was reduced with tin chloride in methanol at reflux for 2 h. The solution was poured over ice and neutralized with saturated sodium bicarbonate. The mixture was extracted with methylene chloride, dried (MgSO4), and concentrated. The oil was purified by silica gel chromatography eluted with hexane/ethyl acetate(9:1 to 8:2) to yield the title compound (0.81 g).

1H NMR (400 mHz, CDCl$_3$ ) d 7.0 (d, 1H), 6.7 (s, 1H), 6.5 (d, 1H), 3.74 (s, 2H), 3.68 (s, 3H), 3.63 (s, 2H)

INTERMEDIATE 38

2-(4-nitro-5-chloro-2-methyl)phenyl acetic acid methyl ester

4-Chloro-2-fluoro-5-nitrotoluene (1.0 g) and dimethylmalonate (0.61 mL) were dissolved in N-methylpyrrolidinone (40 mL). Sodium hydroxide (0.45 g) was added and the solution heated at 80° for 4 h. Reaction was cooled and 1 N hydrochloric acid added. The mixture was extracted with ethyl acetate and concentrated to give 1.52 g of crude product (96%). The above product was dissolved in DMSO and lithium chloride (0.45 g), and water (0.90 mL) were added. The mixture was heated to 100° C. for 4 h. and allowed to stir at room temperature for 18 h. Hydrochloric acid (1 N) was added and the solution extracted with ethyl acetate, dried, filtered, concentrated and the residue purified by chromatography on silica gel to give the title compound as an oil (0.53 g)

INTERMEDIATE 39

(4-Amino-2-chloro-5-methyl-phenyl)-acetic acid methyl ester (4-nitro-2-chloro-5-methyl)phenyl acetic acid methyl ester was reduced with tin chloride in ethanol at 70° C. for 1 h. The solution was cooled and poured over ice and neutralized with saturated sodium bicarbonate. The mixture was extracted with ethyl acetate, dried, and concentrated. The resulting oil was purified by silica gel chromatography eluting with hexane/ethyl acetate(9:1) to yield the title compound (0.446 g). Analysis by NMR indicated a mixture of methyl and ethyl esters.

$^1$H NMR (400 mHz, CDCl$_3$) d 7.09 (s, 1H), 6.57 (s, 1H), 4.1 (q), 3.66 (s, 2H), 3.46 (d), 2.17 (s, 3H), 1.2 (t)

INTERMEDIATE 40

2-(4-amino-3-trifluoromethyl-phenyl]-malonic acid methyl ester

To a solution of benzylmethyl malonate (0.99 g) in anhydrous N,N-dimethylformamide (50 mL) was added 60% NaH in mineral oil (0.18 g) in portions. After 20 min, 4-fluoro-2-trifluoromethylnitrobenzene (1.0 g) in N,N-dimethylformamide (20 mL) was added dropwise via addition funnel. Following the addition, the mixture was heated at 90° C. for 3 h. The mixture was allowed to cool to ambient temperature, and diluted with water. The mixture was extracted with ethyl acetate and the combined organic layers were dried over Na$_2$SO$_4$, filtered and concentrated to give the intermediate benzyl methyl ester as an orange oil. This material was stirred under 1 atmosphere hydrogen gas in 30 mL methanol with 0.20 b 10% Pd/C catalyst for 4.5 h. Filtration through a pad of celite and concentration of the filtrate afforded the title compound (340 mg) as a red oil.

$C_{10}H_{10}F_3N_1O_2$: M-H 232

INTERMEDIATE 41

[4-(2R-Amino-propylamino)-3-trifluoromethyl-phenyl]-acetic acid methyl ester

A mixture of 2-(4-amino-3-trifluoromethyl-phenyl)-malonic acid methyl ester (356 mg), (2R)-(–)-tert-butyoxycarbonyl-amino-1-propionaldehyde (341 mg) and acetic acid (3 drops) in anhydrous dichloromethane (20 mL) was stirred for 10 min. Sodium triacetoxyborohydride (780 mg) was added, and the mixture was stirred at ambient temperature for 24 h. The mixture was diluted with dichloromethane and washed with saturated aqueous sodium bicarbonate. The organic layer was dried over anhydrous Na$_2$SO$_4$, and concentrated. The residue was purified by chromatography eluting with hexane: ethyl acetate (5:1) to afford a pale yellow oil. Concentration of the relevant fractions gave a material which was dissolved in dichloromethane (40 mL) and trifluoroacetic acid (4 mL). The mixture was stirred at ambient temperature for 3 h, and concentrated. The residue was partitioned between aqueous sodium acetate and ethyl acetate. The ethyl acetate layer was concentrated to afford a residue which was purified by silica gel chromatography eluting with ethyl acetate: methanol (5:1) to afford, after concentration of the relevant fractions, the title compound (242 mg) as a yellow oil.

$C_{13}H_{17}N_2O_2F_3$: MH$^+$ 291

INTERMEDIATE 42

(4-{2R-[2-(3-Chloro-phenyl)-2R-hydroxy-ethylamino]-propylamino}-3-trifluoromethyl-phenyl)-acetic acid methyl ester A mixture of [4-(2R-amino-propylamino)-3-trifluoromethyl-phenyl]-acetic acid methyl ester (255 mg) and (R)-3-chlorostyrene oxide (90 mg) was in nitromethane (4 mL) was heated at 105° C. for 36 h. The mixture was allowed to cool to ambient temperature, and concentrated to afford a residue which was purified by silica gel chromatography eluting with hexane: ethyl acetate (2:1) followed by 1:1 hexanes: ethyl acetate to afford after concentration of the relevant fractions the title compound (75.1 mg) as a tan oil.

$C_{21}H_{24}$ Cl $F_3N_2O_3$: MH$^+$ 445

INTERMEDIATE 43

(4-Nitro-2,6-difluoro-phenoxy)-acetic acid methyl ester

A mixture of 4-nitro-2,6-difluoro-phenol (5.08 g, 29.0 mmol) and cesium carbonate (10.3 g, 31.7 mmol) in 100 mL acetonitrile was treated with methyl bromoacetate (3.0 mL, 31.7 mmol). The mixture was heated at reflux for 2 h. The mixture was allowed to cool to ambient temperature, and partitioned between water and ethyl acetate. The organic layer was separated and dried over sodium sulfate, filtered, and concentrated to afford material which was purified by silica gel chromatography eluting with hexane: ethyl acetate (2:1). Concentration of the relevant fractions afforded the title compound (6.11 g) as a white solid.

n.m.r (CDCl$_3$): d 3.83 (s, 3H), 4.98 (s, 2H), 7.85–7.98 (m, 2H).

INTERMEDIATE 44

(4-Amino-2,6-difluoro-phenoxy)-acetic acid methyl ester

A slurry of (4-nitro-2,6-difluoro-phenoxy)-acetic acid methyl ester (737 mg, 2.98 mmol) and 10% palladium on carbon (200 mg) in tetrahydrofuran (40 mL) was stirred under 1 atmosphere of hydrogen gas for 7 h. The mixture was flushed with nitrogen, and filtered through a pad of celite to afford the title compound as a pale tan oil (646 mg) that solidified on standing.

n.m.r (CDCl$_3$): d 3.68 (bs, 2H), 3.78 (s, 3H), 4.59 (s, 2H), 6.17–6.21 (m, 2H).

EXAMPLE 1

(1-{2-[2-(3-Chloro-phenyl)-2R-hydroxyl-ethylamino]-propyl}-2,3-dihydro-1H-indol-5-yl)-acetic acid

[1-(2-{tert-Butoxycarbonyl-[2R-(tert-butyl-dimethyl-silanoxy)-2-(3-chloro-phenyl)-ethyl]-amino}-propyl-2,3-dihydro-1H-indol-5-yl]-acetic acid methyl ester (0.20 g) was dissolved in tetrahydrofuran (5 ml) and the solution was treated with 6N hydrochloric acid (5 ml) for 72 h. The solution was evaporated to dryness and the residue purified by chromatography with Sorbsil C60 eluting with the chloroform:methanol:0.880 ammonium hydroxide (10:5:1) to give the title compound as a yellow solid (0.08 g).

Assay Found: C 61.0; H 6.5; N 6.8% $C_{21}H_{25}ClN_2O_3$.1.25H$_2$O requires C 61.3; H 6.7; N 6.8% n.m.r. (DMSO-d$_6$): d values include 1.05 (m, 3H), 2.61–3.30 (m, 5H), 4.70 (m, 1H), 6.41 (m, 1H), 6.85–6.95 (m, 2H), 7.25–7.45 (m, 4H).

Similarly prepared were:

EXAMPLE 2

(1-{2-[2-(3-Chloro-phenyl)-2R-hydroxyl-ethylamino]-propyl}-1 2,3,4-tetrahydro-quinolin-6-yl)-acetic acid as a brown solid (0.23 g), Assay Found: C 65.2; H 6.95; N 6.9% $C_{22}H_{27}ClN_2O_3$.0.1H$_2$O requires C 65.3; H 6.8; N 6.9% n.m.r. (DMSO-d$_6$): d values include 0.99 (d, 3H), 3.30 (s, 2H), 4.61 (t, 1H), 6.50 (d, 1H), 6.73 (s, 1H), 6.81 (dd, 1H), 7.37 (broad s, 1H).

from [1-(2-{tert-Butoxycarbonyl-[2R-(tert-butyl-dimethyl-silanoxy)-2-(3-chloro-phenyl)-ethyl]-amino}-propyl)-1,2,3,4-tetrahydro-quinolin-6-yl]-acetic acid methyl ester (0.51 g).

EXAMPLE 3

(4-{2R-[2-(3-Chloro-phenyl)-2R-hydroxyl-ethylamino]-propylamino}-2-methyl-phenyl)-acetic acid as a colourless solid (0.08 g), Assay Found: C 55.5; H 6.7; N 8.7% $C_{20}H_{25}ClN_2O_3$.1H$_2$O.0.75NH$_4$Cl requires C 55.2; H 6.95; N 8.85% n.m.r. (DMSO-d$_6$): d values include 1.06 (d, 3H), 2.11 (s, 3H), 4.62 (t, 1H), 6.34 (t, 2H), 6.87 (d, 1H), 7.22–7.50 (m, 4H).

from [4-(2R-{tert-Butoxycarbonyl-[2R-(tert-butyl-dimethyl-silanoxy)-2-(3-chloro-phenyl)-ethyl]-amino}-propylamino)-2-methyl-phenyl]-acetic acid methyl ester (0.2 g).

EXAMPLE 4

(4-{2R-[2-(3-Chloro-phenyl)-2R-hydroxyl-ethylamino]-propylamino}-3-methyl-phenyl)-acetic acid as a colourless solid (0.11 g), Assay Found: C 45.45; H 6.95; N 11.1% $C_{20}H_{25}ClN_2O_3$.2.6H$_2$O.3.3NH$_4$Cl requires C 45.3; H 6.9; N 11.2% n.m.r. (DMSO-d$_6$): d values include 1.10 (d, 3H), 2.02 (s, 3H), 4.71 (t, 1H), 6.49 (d, 1 H), 6.88 (broad d, 2H), 7.21–7.49 (m, 4H).

from [4-(2R-{tert-butoxycarbonyl-[2R-(tert-butyl-dimethyl-silanoxy)-2-(3-chloro-phenyl)-ethyl]-amino}-propylamino)-3-methyl-phenyl]-acetic acid methyl ester (0.24 g).

EXAMPLE 5

(4-{2R-[2-(3-Chloro-phenyl)-2R-hydroxyl-ethylamino]-propylamino}-2-fluoro-phenyl)-acetic acid as a colourless solid (0.08 g), Assay Found: C 49.1; H 5.9; N 9.65% $C_{19}H_{22}ClFN_2O_3$.0.8H$_2$O.1.3NH$_4$Cl requires C 49.1; H 6.25; N 9.9% n.m.r. (DMSO-d$_6$): d values include 1.08 (d, 3H), 4.67 (t, 1H), 6.26–6.42 (m, 2H), 6.96 (t, 1H), 7.23–7.49 (m, 4H).

from [4-(2R-{tert-butoxycarbonyl-[2R-(tert-butyl-dimethyl-silanoxy)-2-(3-chloro-phenyl)-ethyl]-amino}-propylamino)-2-fluoro-phenyl]-acetic acid methyl ester (0.24 g).

EXAMPLE 6

(4-{2R-[2-(3-Chloro-phenyl)-2R-hydroxyl-ethylamino]-propylamino}-3-fluoro-phenyl)-acetic acid as a pale brown foam (0.36 g), Assay Found: C 56.8; H 5.8; N 7.3% $C_{19}H_{22}ClFN_2O_3$.H$_2$O requires C 57.2; H 6.1; N 7.0% n.m.r. (DMSO-d$_6$): d values include 1.08 (d, 3H), 4.71 (t, 1H), 6.66 (t, 1H), 6.79–7.02 (q, 2H), 7.21–7.51 (m, 4H).

from [4-(2R-{tert-butoxycarbonyl-[2R-(tert-butyl-dimethyl-silanoxy)-2-(3-chloro-phenyl)-ethyl]-amino}-propylamino)-3-fluoro-phenyl]-acetic acid methyl ester (0.50 g).

EXAMPLE 7

(4-{2R-[2-(3-Chloro-phenyl)-2R-hydroxyl-ethylamino]-propylamino}-2,3-difluoro-phenyl)-acetic acid as a colourless solid (0.20 g), Assay Found: C 37.2; H 6.4; N 11.4% $C_{19}H_{21}ClF_2N_2O_3.3H_2O.3NH_4Cl$ requires C 37.1; H 6.2; N 11.9% n.m.r. (DMSO-$d_6$): d values include 1.14 (d, 3H), 5.02 (t, 1H), 6.67 (broad t, 1H), 6.90 (t, 1H), 7.28–7.60 (m, 4H)

from [4-(2R-{tert-butoxycarbonyl-[2R-(tert-butyl-dimethyl-silanoxy)-2-(3-chloro-phenyl)-ethyl]-amino}-propylamino)-2,3-difluoro-phenyl]-acetic acid methyl ester (0.44 g).

EXAMPLE 8

(5-Chloro-4-{2R-[2-(3-chloro-phenyl)-2R-hydroxy-ethylaminol-propylamino}-2-methoxy-phenyl)-acetic acid dihydrochloride as a colourless solid (0.006 g)

n.m.r. (DMSO-$d_6$): d values include 1.04 (s, 3H), 3.68 (s, 3H), 4.65 (t, 1H), 7.00 (s, 1H), 7.21–7.35 (m, 4H), 7.39 (s, 1H)

from (5-chloro-[4-(2R-{tert-butoxycarbonyl-[2R-(tert-butyl-dimethyl-silanoxy)-2-(3-chloro-phenyl)-ethyl]-amino}-propylamino)-2-methoxy-phenyl])-acetic acid methyl ester (0.037 g).

EXAMPLE 9

(4-{2-[2-(3-chloro-phenyl)-2R-hydroxyl-ethylamino]-ethylamino}-2-methyl-phenyl)-acetic acid as a colourless solid (0.287 g)

$C_{19}H_{24}Cl N_2O_3$: MH+ 363.1470 (error 1.6 ppm)

n.m.r. (DMSO-$d_6$): d values include 2.11 (s, 3H), 4.65 (m, 1H), 6.32 (dd, 1H), 6.34 (d, 1H), 6.84 (d, 1H), 7.40 (broad s, 1H)

from 4-(2-(tert-Butoxycarbonyl-[2R-(tert-butyl-dimethyl-silanyloxy)-2-(3-chloro-phenyl)-ethyl]-amino}-ethylamino)-2-methyl-phenyl]-acetic acid methyl ester (0.549 g)

EXAMPLE 10

(4-{2-[2-(3-chloro-phenyl)-2R-hydroxyl-ethylamino]-ethylamino}-2-trifluoromethyl-phenyl)-acetic acid as a yellow solid (0.028 g)

$C_{19}H_{21}Cl F_3N_2O_3$: MH+ 417.1208 (error 3.6 ppm)

n.m.r. (DMSO-$d_6$): d values include 3.54 (s, 2H), 4.68 (m, 1H), 6.76 (dd, 1H), 6.84 (d, 1H), 7.15 (d, 1H), 7.41 (broad s, 1H)

from [4-(2-{tert-Butoxycarbonyl-[2R-(tert-butyl-dimethyl-silanyloxy)-2-(3-chloro-phenyl)-ethyl]-amino}-ethylamino)-2-trifluoromethyl-phenyl]-acetic acid methyl ester (0.18 g).

EXAMPLE 11

(4-{2-[2-(3-chloro-phenyl)-2R-hydroxyl-ethylamino]-ethylamino}-2,3-difluoro-phenyl)-acetic acid from [4-(2-{tert-Butoxycarbonyl-[2R-(tert-butyl-dimethyl-silanyloxy)-2-(3-chloro-phenyl)-ethyl]-amino}-ethylamino)-2,3-difluoro-phenyl]-acetic acid methyl ester.

EXAMPLE 12

(4-{2R-[2-(3-Chloro-phenyl)-2R-hydroxyl-ethylamino]-amino}-2,3,6-trifluoro-phenyl)-acetic acid from [4-(2R-{tert-Butoxycarbonyl-[2R-(tert-butyl-dimethyl-silanyloxy)-2-(3-chloro-phenyl)-ethyl]-amino}-propylamino)-2,3,6-trifluoro-phenyl]-acetic acid methyl ester.

EXAMPLE 13

[2-Chloro-4-(2R-{[2-(3-chloro-phenyl)-2R-hydroxy-ethyl]-amino}-propylamino)-phenyl]-acetic acid (15 mg) as a white solid.

$^1$H NMR (300 mHz, DMSO-$d_6$) d 7.4(s,$_1$H), 7.3 (m,3H), 7.0 (d, 1H), 6.6 (s, 1H), 6.5 (d, 1H), 5.8 (bs, 1H), 4.7 (m,1 H), 1.1 (d, 3H).

HPLC analysis (C18 column) 1mL/min, 20–50% acetonitrile/water( 0.1% TFA) $T_R$=17.5 min from [4-(2R-{tert-Butoxycarbonyl-[2R-(tert-butyl-dimethyl-silanyioxy)-2-(3-chloro-phenyl)-ethyl]-amino}-propylamino)-2-chloro-phenyl]-acetic acid methyl ester.

EXAMPLE 14

[5-Chloro-4-(2R-{[2-(3-chloro-phenyl)-2R-hydroxy-ethyl]-amino}-propylamino)-2-methyl-phenyl]-acetic acid methyl ester as a white solid (110 mg)

Analysis: Calc. for $C_{20}H_{24}N_2O_3Cl_2(0.25 H_2O)$: C, 56.55, H, 5.69, N, 6.59% Found: C, 56.49, H, 5.99, N, 6.56% $C_{20}H_{24}N_2O_3Cl_2$: MH+ 411 from [4-(2R-{tert-Butoxycarbonyl-[2R-(tert-butyl-dimethyl-silanyloxy)-2-(3-chloro-phenyl)-ethyl]-amino}-propylamino)-5-chloro-2-methyl-phenyl]-acetic acid methyl ester.

EXAMPLE 15

(4-{2R-[2-(3-Chloro-phenyl)-2R-hydroxy-ethylamino]-propylamino}-2,6-difluoro-phenoxy)-acetic acid as an off-white solid (46 mg)

mp 105° C. (dec)

n.m.r (CDCl3): d 1.34 (d, 3H), 3.05–3.57 (m, 5H), 4.30 (s, 2H), 5.00 (dd, 1H), 6.20–6.30 (m, 2H), 7.28–7.40 (m, 3H), 7.47 (s, 1H).

from (4-[2R-{tert-butoxycarbonyl-[2R-(tertbutyl-dimethyl-silanyloxy)-2-(3-chloro-phenyl)-ethyl]-amino}-propylamino)-2,6-difluoro-phenyoxy]-acetic acid methyl ester (451 mg)

EXAMPLE 16

(4-{2R-[2-(3-Chloro-phenyl)-2R-hydroxy-ethylamino]-propylamino}-3-trifluoromethyl-phenyl)-acetic acid A solution of (4-{2R-[2-(3-chloro-phenyl)-2R-hydroxy-ethylamino]-propylamino}-3-trifluoromethyl-phenyl)-acetic acid methyl ester (75.1 mg) in tetrahydrofuran (4 mL) and 6N aqueous hydrochloric acid (4 mL) was stirred at ambient temperature for 18 h. The residue was concentrated and lyophilized to afford a residue which was purified by silica gel chromatography eluting with chloroform:methanol:concentrated ammonium hydroxide (30:15:1) to afford after concentration of the relevant fractions the title compound (58.9 mg) as a white solid.

mp 161–163° C.

Assay: Found: C 54.5, H. 5.2, N, 6.1% $C_{20}H_{22}Cl_1F_3N_2O_3.0.5H_2O$ requires C 54.6, H. 5.3, N. 6.4%

EXAMPLE 17

(4-{2R-[2-(3-Chloro-Phenyl)-2R-hydroxy-ethylamino]-propylamino}-2-triftuoromethyl-phenyl)-acetic acid A solution of (4-{2R-[2-(3-chloro-phenyl)-2R-hydroxy-ethylamino]-propylamino}-2-trifluoromethyl-phenyl)- acetic acid methyl ester (290 mg) in tetrahydrofuran (4 mL) and 6N aqueous hydrochloric acid (4 mL) was stirred at ambient temperature for 18 h. The residue was concentrated and lyophilized to afford a residue which was purified by silica gel chromatography eluting with chloroform:methanol:concentrated ammonium hydroxide (30:15:1) to afford after concentration of the relevant fractions the title compound (122 mg) as a white solid.

$C_{20}H_{22}Cl_1F_3N_2O_3$ MH$^+$ 431.134 (error 2.2 ppm)

n.m.r (CDCl$_3$): d values include 1.085 (d, 3H), 2.85 (m, 2H), 2.885–3.12 (m, 3H), 3.545 (s, 2H) 4.705 (m, 1H), 6.045 (bt, 1H), 6.765 (dd, 1H), 6.855 (d, 1H), 7.265–7.4 (m, 3H).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| | Direct Compression Tablet | mg/tablet |
|---|---|---|
| (i) | Active Ingredient | 4.688 |
| | Calcium Hydrogen Phosphate BP* | 83.06 |
| | Croscarmellose Sodium NF | 1.8 |
| | Magnesium Stearate BP | 0. |
| | Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| | | mg/tablet |
|---|---|---|
| (ii) | Active Ingredient. | 0.31 |
| | Anhydrous Lactose USNF | 131.99 |
| | Pregelatinised Starch USNF | 7.0 |
| | Magnesium Stearate BP | 0.7 |
| | Compression weight | 140.0 |

The active ingredient is passed through a 60 mesh sieve, and blended with the lactose, pregelatinised starch and magnesium stearate. The resultant mix is compressed into tablets using a Manesty F3 tablet machine fitted with 7.5 mm normal concave punches.

SYRUP

This may be either a sucrose or sucrose free presentation.

| A. | Sucrose Syrup | mg/5 ml dose |
|---|---|---|
| | Active Ingredient | 2.5 |
| | Sucrose BP | 2750.0 |
| | Glycerine BP | 500.0 |
| | Buffer | |
| | Flavour | |
| | Colour | as required |
| | Preservative | |
| | Purified Water BP | 5.0 m |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. | Sucrose-free Syrup | mg/5 ml dose |
|---|---|---|
| | Active Ingredient | 2.5 |
| | Hydroxypropylmethylcellulose USP (viscosity type 4000) | 22.5 |
| | Buffer | |
| | Flavour | |
| | Colour | as required |
| | Preservative | |
| | Sweetener | |
| | Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

INJECTION FOR INTRAVENOUS ADMINISTRATION

| | | μg/ml |
|---|---|---|
| (i) | Active Ingredient | 800 |
| | Dilute Hydrochloric Acid BP to pH 3.5 | |
| | Sodium Chloride Injection BP to 1 ml | |

The active ingredient is dissolved in a suitable volume of Sodium Chloride Injection BP, the pH of the resultant solution is adjusted to pH3.5 with dilute hydrochloric acid BP then the solution is made to volume with sodium chloride injection BP and thoroughly mixed. The solution is filled into Type I clear glass 5 ml ampoules which are sealed under a headspace of air, by fusion of the glass then sterilised by autoclaving at 120° for not less than 15 minutes.

| | | μg/ml |
|---|---|---|
| (ii) | Active ingredient | 56.2 |
| | Sodium Chloride BP | as required |
| | Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

SUPPOSITORY FOR RECTAL ADMINISTRATION

| Active ingredient | 49.0 mg |
|---|---|
| Witepsol* H15 to | 1.0 g |

*a proprietary grade of Adeps Solidus Ph.Eur.

A suspension of the active ingredient in molten Witepsol is prepared and filled using suitable machinery, into 1g size suppository moulds.

The compounds of Examples 7, 8 and 15 were tested for beta-3-adrenoceptor activity using above described Method I with the following results:

| | EPMR | | |
|---|---|---|---|
| Test Method | Ex 7 | Ex 8 | Ex 15 |
| Method 1 | 0.2 | 0.4 | 6.0 |

The protective effect of the compound of Example 7 was measured as described in above Method 2 and an $ED_{50}$ of 0.003 mg/kg was obtained.

We claim:

1. A compound of the general formula (I):

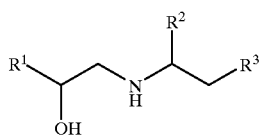

(I)

wherein

R$^1$ represents an aryl group optionally substituted by one or more substituents selected from halogen, hydroxy, C$_{1-6}$alkoxy, C$_{1-6}$alkyl, nitro, cyano, hydroxymethyl and trifluoromethyl;

R$^2$ represents hydrogen or C$_{1-6}$alkyl;

R$^3$ represents a group A

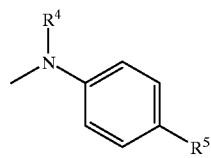

where the ring is substituted by one to four further substituents selected from C$_{1-6}$alkyl, halogen, trifluoromethyl, and C$_{1-6}$alkoxy;

or R$^3$ represents a group B

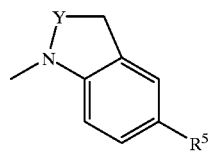

where the aromatic ring is optionally substituted by up to three further substituents selected from C$_{1-6}$alkyl, halogen, trifluoromethyl, and C$_{1-6}$alkoxy;

R$^4$ represents hydrogen, or C$_{1-6}$alkyl;

R$^5$ represents ZCH$_2$CO$_2$H wherein Z represents a bond, or O;

Y represents (CH$_2$), where n is 1–3;

and physiologically acceptable derivatives thereof.

2. A compound as claimed in claim 1 wherein R$^1$ represents a phenyl group substituted by a chlorine atom located in the meta position.

3. A compound as claimed in claim 1 wherein R$^2$ is methyl or H.

4. A compound as claimed in claim 1 where R$^3$ is group A substituted by one or more substituents selected from halogen, methyl, trifluoromethyl, and methoxy.

5. A compound as claimed in claim 1 where R$^3$ is group B, n is 1 or 2, and the aromatic ring is unsubstituted.

6. A compound as claimed in claim 1 where R$^4$ is hydrogen or methyl.

7. A compound as claimed in claim 1 where R$^1$ represents phenyl substituted by a chlorine atom located in the meta position, R$^2$ represents hydrogen or methyl, R$^3$ represents a group A and is substituted by one or more groups selected from halogen, methyl, trifluoromethyl, and methoxy, R$^4$ represents hydrogen or methyl, R$^5$ represents CH$_2$CO$_2$H, and physiologically acceptable derivatives thereof.

8. A compound selected from the group consisting of
(1-{2-[2-(3-chloro-phenyl)-2R-hydroxyl-ethylamino]-propyl}-2,3-dihydro-1H-indol-5-yl)-acetic acid;
(1-{2-[2-(3-chloro-phenyl)-2R-hydroxyl-ethylamino]-propyl}-1,2,3,4-tetrahydro-quinolin-6-yl)-acetic acid;
(4-{2R-[2-(3-chloro-phenyl)-2R-hydroxyl-ethylamino]-propylamino}-2-methyl-phenyl)-acetic acid;
(4-{2R-[2-(3-chloro-phenyl)-2R-hydroxyl-ethylamino]-propylamino}-3-methyl-phenyl)-acetic acid;
(4-{2R-[2-(3-chloro-phenyl)-2R-hydroxyl-ethylamino]-propylamino}-2-fluoro-phenyl)-acetic acid;
(4-{2R-[2-(3-chloro-phenyl)-2R-hydroxyl-ethylamino]-propylamino}-3-fluoro-phenyl)-acetic acid;
(4-{2R-[2-(3-chloro-phenyl)-2R-hydroxyl-ethylamino]-propylamino}-2,3-difluoro-phenyl)-acetic acid;
(5-Chloro-4-{2R-[2-(3-chloro-phenyl)-2R-hydroxy-ethylamino]-propylamino}-2-methoxy-phenyl)-acetic acid;
(4-{2-[2-(3-chloro-phenyl)-2R-hydroxyl-ethylamino]-ethylamino}-2-methyl-phenyl)-acetic acid;
(4-{2-[2-(3-chloro-phenyl)-2R-hydroxyl-ethylamino]-ethylamino}-2,3-difluoro-phenyl)-acetic acid;
(4-{2-[2-(3-chloro-phenyl)-2R-hydroxyl-ethylamino]-ethylamino}-2-trifluoromethyl-phenyl)-acetic acid;
(4-{2R-[2-(3-chloro-phenyl)-2R-hydroxyl-ethylamino]-propylamino}-2,6-difluoro-phenyl)-acetic acid;
(4-{2-[2-(3-chloro-phenyl)-2R-hydroxyl-ethylamino]-ethylamino}-2,3,6-trifluoro-phenyl)-acetic acid;
(4-{2-[2-(3-chloro-phenyl)-2R-hydroxyl-ethylamino]-propylamino}-2-trifluoromethyl-phenyl)-acetic acid;

(4-{2R-[2-(3-Chloro-phenyl)-2R-hydroxyl-ethylamino]-propylamino}-2,3,6-trifluoro-phenyl)-acetic acid;

[2-Chloro-4(2-{[2-(3-chloro-phenyl)-2R-hydroxy-ethyl]-amino}-propylamino)-phenyl]-acetic acid;

[5-Chloro-4-(2R-{[2-(3-chloro-phenyl)-2R-hydroxy-ethyl]-amino}-propylamino)-2-methyl-phenyl]-acetic acid;

(4-{2R-[2-(3-Chloro-phenyl)-2R-hydroxy-ethylamino]-propylamino}-2,6-difluoro-phenoxy)-acetic acid and;

(4-{2R-[2-(3-Chloro-phenyl)-2R-hydroxy-ethylamino]-propylamino}-3-trifluoromethyl-phenyl)-acetic acid;

or a physiologically acceptable derivative thereof.

9. (4-{2R-[2-(3-chloro-phenyl)-2R-hydroxyl-ethylamino]-propylamino}-2,3-difluoro-phenyl)-acetic acid;

or a physiologically acceptable derivative thereof.

10. A method of treatment of a mammal suffering from a condition susceptible of amelioration by an atypical beta-adrenoceptor agonist comprising administration of an effective amount of a compound according to claim 1 or a physiologically acceptable derivative thereof.

11. A pharmaceutical composition comprising a compound according to claim 1 or a physiologically acceptable derivative thereof together with one or more pharmaceutically acceptable carriers.

12. A pharmaceutical composition which comprises a compound according to claim 1 and a non-steroidal anti-inflammatory drug, together with one or more pharmaceutically acceptable carriers.

13. A process for preparing a compound of formula (I) as claimed in claim 1, or a physiologically acceptable derivative thereof which comprises:

(A), compounds of formula (I) may be prepared by reaction of a compound of formula (Ia)

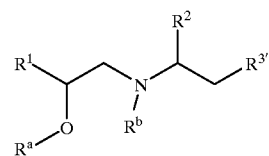

(Ia)

wherein $R^1$, $R^2$, and, are as defined as for formula (I), $R^3$ represents $R^3$ where the acidic group is protected by an alkyl ester, and $R^a$ and $R^b$ are protecting groups, by deprotection of the protecting groups or (B), compounds of formula (I) may be prepared by reaction of a compound of formula (II) with a compound of formula (III):

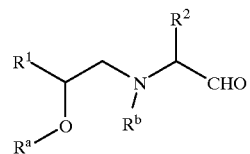

(II)

(III)

wherein $R^1$, $R^2$, $R^3$, $R^a$, and $R^b$ are as defined above, in the presence of a reducing agent, followed by removal of the protecting groups.

* * * * *